United States Patent [19] [11] Patent Number: 5,102,911
Lee et al. [45] Date of Patent: Apr. 7, 1992

[54] 4-SUBSTITUTED HMG-CoA REDUCTASE INHIBITORS

[75] Inventors: Ta Jyh. Lee; Wilbur J. Holtz, both of Lansdale, Pa.

[73] Assignee: Merck & Co, Inc., Rahway, N.J.

[21] Appl. No.: 549,039

[22] Filed: Jul. 6, 1990

Related U.S. Application Data

[62] Division of Ser. No. 363,744, Jun. 9, 1989, Pat. No. 4,970,231.

[51] Int. Cl.$^5$ .................. A61K 31/215; C07C 69/608
[52] U.S. Cl. ........................... 514/510; 560/1; 560/39; 560/31; 560/32; 560/42; 560/45; 560/47; 560/56; 560/49; 560/61; 560/63; 560/29; 560/30; 560/123; 560/121; 560/124; 560/126; 560/125; 560/157; 560/160; 560/161; 560/162; 560/183; 560/184; 560/188; 560/119; 560/256; 546/205; 546/206; 544/387; 548/531; 548/532; 558/428; 519/480; 519/482; 519/824; 519/460; 549/292; 514/255; 514/423; 514/319
[58] Field of Search .................. 560/1, 39, 42, 45, 46, 560/47, 49, 56, 61, 63, 29, 30, 30, 31, 32, 121, 123, 124, 125, 126, 157, 160, 161, 162, 183, 184, 188, 220, 256, 119; 546/205, 206; 544/389; 548/531, 532; 558/428; 514/510, 480, 481, 959, 460, 824, 225, 423, 319; 549/292

[56] References Cited

U.S. PATENT DOCUMENTS

| | | | |
|---|---|---|---|
| 4,448,979 | 5/1984 | Terahara et al. | 549/292 |
| 4,533,859 | 8/1985 | Terahara et al. | 435/146 |
| 4,604,472 | 8/1986 | Ide et al. | 514/824 |
| 4,611,068 | 9/1986 | Guirdon | 549/292 |
| 4,733,003 | 3/1988 | Ide et al. | 549/292 |
| 4,766,145 | 8/1988 | Lee et al. | 549/292 |
| 4,855,456 | 8/1989 | Lee et al. | 549/292 |
| 4,866,090 | 9/1989 | Hoffman et al. | 514/466 |

Primary Examiner—Glennon H. Hollrah
Assistant Examiner—Mark W. Russell
Attorney, Agent, or Firm—Melvin Winokur; Joseph F. DiPrima

[57] ABSTRACT

HMG-CoA reductase inhibitors of formulae (I) and (II) are disclosed.

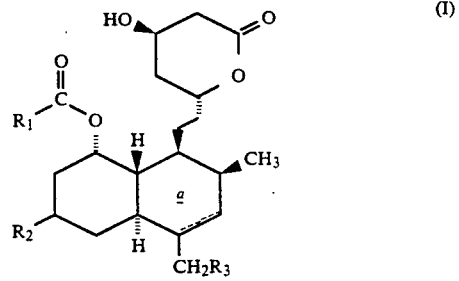

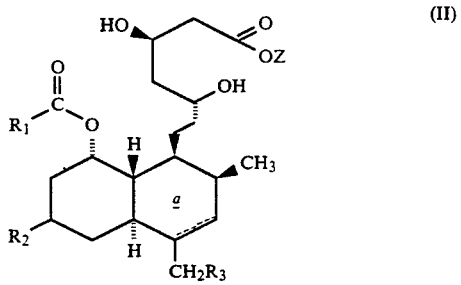

9 Claims, No Drawings

4-SUBSTITUTED HMG-COA REDUCTASE INHIBITORS

This is a division of application Ser. No. 363,744, filed June 9, 1989 now U.S. Pat. No. 4,970,231.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that function by limiting cholesterol biosynthesis by inhibiting the enzyme, HMG-CoA reductase. In addition to the natural fermentatio products, mevastatin and lovastatin, there are a variety of semi-synthetic and totally synthetic analogs thereof.

The naturally occurring compounds and their semi-synthetic analogs have the following general structural formulae:

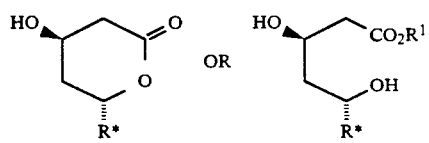

wherein:
$R^1$ is hydrogen, $C_{1-5}$ alkyl or $C_{1-5}$ alkyl substituted with a member of the group consisting of phenyl, dimethylamino, or acetylamino.

U.S. Pat. No. 4,517,373 discloses semisynthetic hydroxy containing compounds represented by the above general formula wherein $R^*$ is

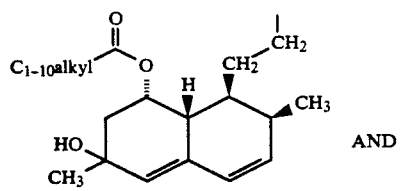

AND

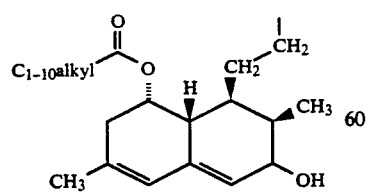

U.S. Pat. No. 4,537,859 and U.S. Pat. No. 4,448,979 also disclose semi-synthetic hydroxy-containing compounds represented by the above general formula wherein $R^*$ is

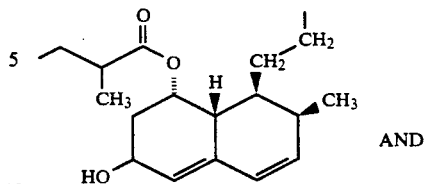

AND

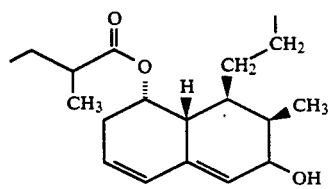

These compounds are prepared by the action of certain microorganisms on the corresponding non-hydroxylated substrates. One such organism described in U.S. Pat. No. 4,537,859 is of the genus Nocardia.

U.K. Patent 2,075,013 discloses semi-synthetic hydroxy containing compounds represented by the above general formula wherein $R^*$ is:

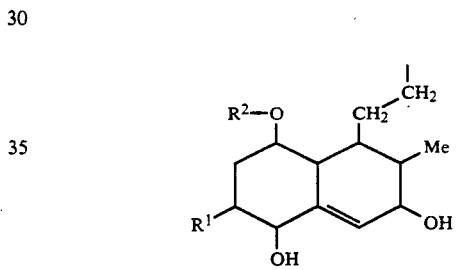

wherein $R^1$ is H or Me, and $R^2$ is H or acyl.

U.S. Patent application Ser. No. 254,525 filed Oct. 6, 1988 discloses 6-substituted compounds of the above general formula wherein $R^*$ is:

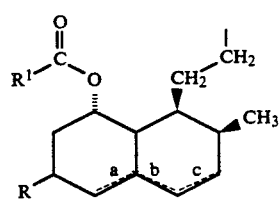

wherein R is CH₂OH,

and $R^1$, $R^4$, $R^7$, $R^8$ and $R^9$ are broadly defined organic moieties.

U.S. Pat. Nos. 4,604,472 and 4,733,003 disclose compounds of the above formula wherein $R^*$ is:

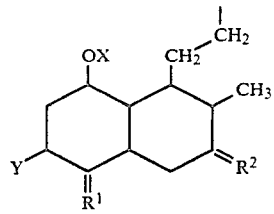

wherein X represents a hydrogen atom or a 2-methylbutyryl group, Y represents a hydrogen atom or a methyl group and $R^1$ and $R^2$ are the same or different and each represents an oxygen atom or a group of formula =N—$OR^3$ where $R^3$ is a hydrogen or alkyl moiety.

Copending U.S. Patent application Ser. No. 213,010 filed June 29, 1988 discloses 5-oxygenated compounds of the above general formula wherein R* is

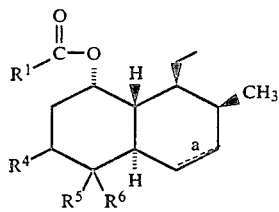

$R^4$ is H, alkyl or substituted alkyl and $R^5$ and $R^6$ are H, OH or $OR^7$ where $R^7$ represents a phosphoryl or acyl moiety.

Copending U.S. Patent application Ser. No. 161,579 filed Feb. 29, 1988 discloses epoxide containing compounds wherein R* is:

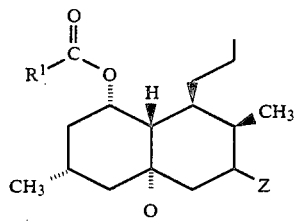

Z is I, Br or Cl.

Copending U.S. Patent application Ser. No. 161,529 filed Feb. 29, 1988 discloses hydroxy containing compounds of the above general formula wherein R* is:

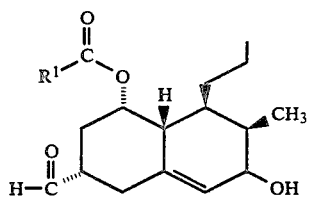

DETAILED DESCRIPTION OF THE INVENTION

This invention relates to HMG-CoA reductase inhibitors of formulae (I) and (II):

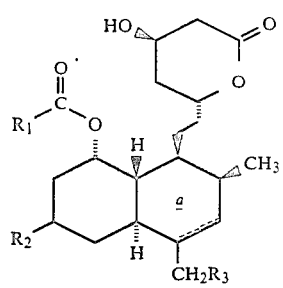

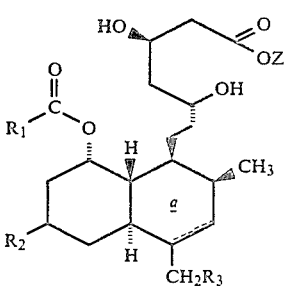

wherein:
$R_1$ is:
(1) $C_{1-10}$ alkyl;
(2) substituted $C_{1-10}$ alkyl in which one or more substituent(s) is
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y,
 (i) $C_{1-10}$ alkylS(O)$_n$,
 (j) $C_{3-8}$ cycloalkylS(O)$_n$,
 (k) phenylS(O)$_n$,
 (l) substituted phenylS(O)$_n$ in which the substituents are X and Y, and
 (m) oxo,
 (n) nitrile,
 (o) $NR_4R_5$,
 (p) $CONR_4R_5$;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is
 (a) $C_{1-10}$ alkyl
 (b) substituted $C_{1-10}$ alkyl in which the substituent is
  (i) halogen,
  (ii) hydroxy,
  (iii) $C_{1-10}$ alkoxy,
  (iv) $C_{1-5}$ alkoxycarbonyl,
  (v) $C_{1-5}$ acyloxy,
  (vi) phenyl,
  (vii) substituted phenyl in which the substituents are X and Y
  (viii) $C_{1-10}$ alkylS(O)$_n$,
  (ix) $C_{3-8}$ cycloalkylS(O)$_n$,
  (x) phenylS(O)$_n$, (xi) substituted phenylS(O)$_n$ in which the substituents are X and Y, and
(xii) oxo,
(c) C$_{1-10}$ alkylS(O)$_n$,
(d) C$_{3-8}$ cycloalkylS(O)$_n$,
(e) phenylS(O)$_n$,
(f) substituted phenylS(O)$_n$ in which the substituents are X and Y,
(g) halogen,
(h) hydroxy,
(i) C$_{1-10}$ alkoxy,
(j) C$_{1-5}$ alkoxycarbonyl,
(k) C$_{1-5}$ acyloxy,
(l) phenyl, and
(m) substituted phenyl in which the substituents are X and Y;
(7) phenyl;
(8) substituted phenyl in which the substituents are X and Y;
(9) amino;
(10) C$_{1-5}$ alkylamino;
(11) di(C$_{1-5}$ alkyl)amino;
(12) phenylamino;
(13) substituted phenylamino in which the substituents are X and Y;
(14) phenyl C$_{1-10}$ alkylamino;
(15) substituted phenyl C$_{1-10}$ alkylamino in which the substituents are X and Y;
(16) a member selected from the group consisting of:
  (a) piperidinyl,
  (b) pyrrolidinyl,
  (c) piperazinyl;
R$_2$ is H or CH$_3$;
R$_3$ is selected from:
  (a) hydrogen,
  (b) halogen,
  (c) hydroxy,
  (d) C$_{1-5}$ alkyl,
  (e) substituted C$_{1-5}$ alkyl in which the substituent is selected from:
    (1) OH,
    (2) halogen,
    (3) trifluoromethyl,
    (4) C$_{1-3}$ alkoxy,
    (5) C$_{1-3}$ alkylcarbonyloxy,
    (6) phenylcarbonyloxy,
    (7) C$_{1-3}$ alkoxycarbonyl,
    (8) phenyloxycarbonyl,
    (9) NR$_4$R$_5$,
    (10) CONR$_4$R$_5$;
  (f) C$_{2-6}$ alkenyl,
  (g) phenyl substituted with X and Y,
  (h) C$_{1-5}$ alkylS(O)$_n$,
  (i) phenylS(O)$_n$,
  (j) C$_{1-3}$ alkoxycarbonyl,
  (k) NR$_4$R$_5$,
  (l) CONR$_4$R$_5$,
  (m) C$_{1-3}$ alkoxy,
  (n) C$_{1-3}$ alkylcarbonyloxy,
  (o) phenylcarbonyloxy;
R$_4$ and R$_5$ are independently selected from:
  (a) C$_{1-5}$alkyl
  (b) substituted phenyl in which the substituents are X and Y;
X and Y are independently selected from:
  (a) OH,
  (b) halogen,
  (c) trifluoromethyl,
  (d) C$_{1-3}$alkoxy,
  (e) C$_{1-3}$alkylcarbonyloxy,
  (f) phenylcarbonyloxy,
  (g) C$_{1-3}$alkoxycarbonyl,
  (h) phenyloxycarbonyl,
  (i) hydrogen,
  (j) C$_{1-5}$alkyl;
Z is selected from
  (1) hydrogen;
  (2) C$_{1-5}$alkyl;
  (3) substituted C$_{1-5}$ in which the substituent is selected from
    (a) phenyl,
    (b) dimethylamino, and
    (c) acetylamino, and
  (4) 2,3-dihydroxypropyl;
a is a single bond or a double bond; halogen is Cl or F; n is 0, 1 or 2; or a pharmaceutically acceptable salt thereof.

Except where specifically defined to the contrary, the terms "alkyl", "alkenyl", "acyl" "aryloxy" and "alkoxy" include both the straight-chain and branched-chain species of the term.

One embodiment of this invention is the class of compounds of formulae (I) and (II) wherein:
R$_1$ is selected from:
  (1) C$_{1-10}$ alkyl;
  (2) substituted C$_{1-10}$ alkyl in which one or more substituent(s) is selected from
    (a) halogen,
    (b) hydroxy,
    (c) C$_{1-10}$ alkoxy,
    (d) C$_{1-5}$ alkoxycarbonyl,
    (e) C$_{1-5}$ acyloxy,
    (f) C$_{3-8}$ cycloalkyl,
    (g) phenyl,
    (h) substituted phenyl in which the substituents are X and Y,
    (i) C$_{1-10}$ alkylS(O)$_n$,
    (j) nitrile,
    (k) NR$_4$R$_5$,
    (l) CONR$_4$R$_5$,
    (m) oxo;
  (3) C$_{3-8}$ cycloalkyl;
  (4) substituted C$_{3-8}$ cycloalkyl in which one substituent is selected from
    (a) C$_{1-10}$ alkyl,
    (b) substituted C$_{1-10}$ alkyl in which the substituent is selected from
      (i) halogen,
      (ii) hydroxy,
      (iii) C$_{1-10}$ alkoxy
      (iv) C$_{1-5}$ acyloxy,
      (v) C$_{1-5}$ alkoxycarbonyl,
      (vi) phenyl,
      (vii) substituted phenyl in which the substituents are X and Y, and
      (viii) oxo,
    (c) halogen,
    (d) hydroxy,
    (e) C$_{1-10}$ alkoxy,
    (f) C$_{1-5}$ alkoxycarbonyl,
    (g) C$_{1-5}$ acyloxy,
    (h) phenyl,
    (i) substituted phenyl in which the substituents are X and Y;
  (5) phenylamino;

(6) substituted phenylamino in which the substituents are X and Y;
(7) phenylC$_{1-10}$alkylamino; and
(8) substituted phenyl C$_{1-10}$ alkylamino in which the substituents are X and Y,
(9) C$_{2-10}$ alkenyl;

R$_3$ is:
(a) hydrogen;
(b) hydroxy,
(c) C$_{1-5}$ alkyl,
(d) substituted C$_{1-5}$ alkyl in which the substitutent is selected from:
(1) OH,
(2) C$_{1-3}$ alkoxy,
(3) C$_{1-3}$ alkylcarbonyloxy,
(4) phenylcarbonyloxy,
(5) C$_{1-3}$ alkoxycarbonyl,
(6) phenyloxycarbonyl;
(e) phenyl substituted with X and Y;
(f) C$_{1-3}$ alkoxy,
(g) C$_{1-3}$ alkylcarbonyloxy,
(h) phenylcarbonyloxy.

X and Y independently are:
(a) OH,
(b) F,
(c) trifluoromethyl,
(d) C$_{1-3}$ alkoxy,
(e) hydrogen,
(f) C$_{1-5}$ alkyl.

In one class of this embodiment ar the compounds of formulae (I) and (II) wherein:
R$_1$ is C$_{1-10}$ alkyl;
R$_2$ is CH$_3$, and
R$_3$ is:
(a) hydrogen,
(b) C$_{1-5}$ alkyl,
(c) substituted C$_{1-5}$ alkyl in which the substitutent is selected from:
(1) C$_{1-3}$ alkoxycarbonyl,
(2) hydroxy,
(3) oxo;

Exemplifying this class are the following compounds:

(1) 6(R)-[2-[8(S)-(2,2-dimethylbutyryloxy) -2(S),4,6(S)-trimethyl-1,2,4a(S),5,6,7,8,8a(R)-octahydronaphthyl -1-(S)]ethyl]-4(R)-hydroxy-3,4,5,6-tetrahydro -2H-pyran-2-one.

(2) 6(R)-[2-[4-(2-ethoxycarbonyl)ethyl-8(S) -(2,2-dimethylbutyryloxy)-2(S),6(S)-dimethyl-1,2,4a -(S),5,6,7,8,8a(R)-octahydronaphthyl-1(S)]ethyl]- 4(R) -hydroxy-3,4,5,6-tetrahydro-2H-pyran-2-one.

(3) 6(R)-[2-[8(S)-(2-methylbutyryloxy)-2(S) -4,6(S)-trimethyl-1,2,4a(S),5,6,7,8,8a(R)-octahydronaphthyl -1(S)]ethyl]-4(R)-hydroxy-3,4,5,6-tetrahydro -2H-pyran-2-one.

(4) 6(R)-[2-[4-(2-ethoxycarbonyl)ethyl-8(S) -(2-methylbutyryloxy)-2(S),6(S)-dimethyl-1,2,4a(S),5,6,7,8- ,8a(R) -octahydronaphthyl-1(S)]ethyl]-4(R) -hydroxy-3,4,5,6-tetrahydro-2H-pyran-2-one.

The compounds of formula (I) are prepared from lovastatin, simvastatin or mevastatin following the outline in Schemes 1 and 2.

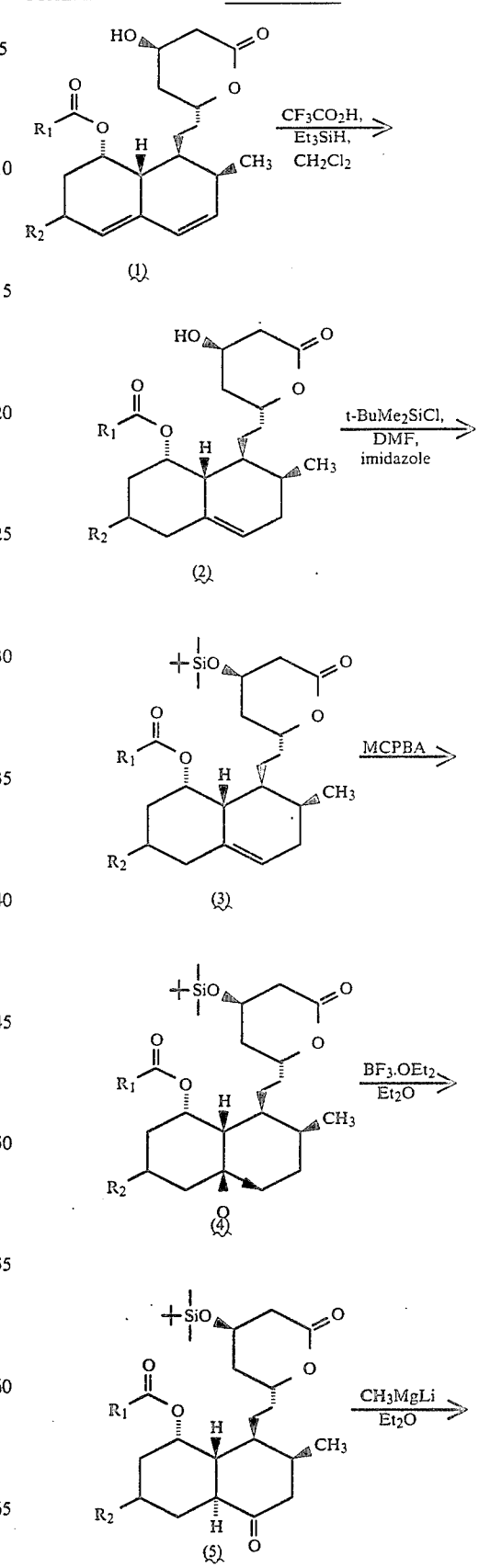

SCHEME 1

SCHEME 1 -continued

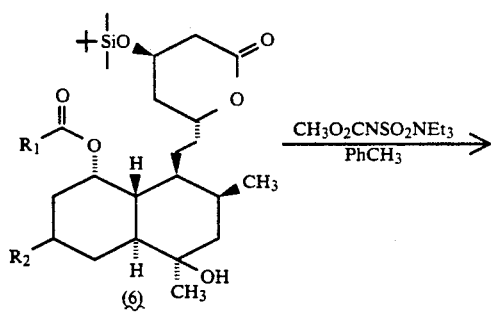

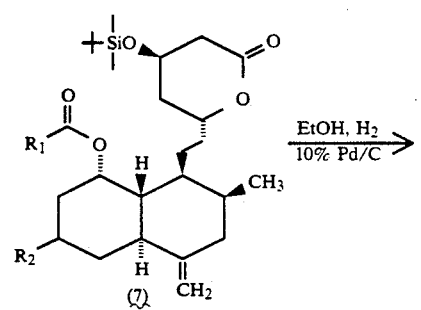

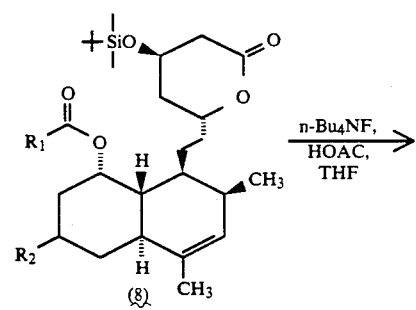

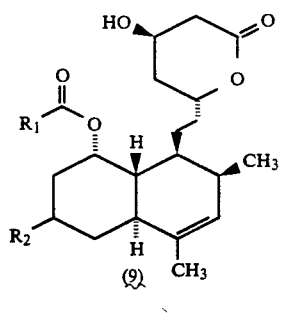

SCHEME 2

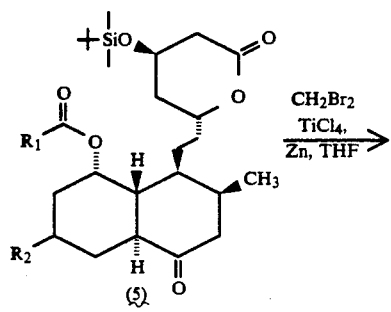

-continued SCHEME 2

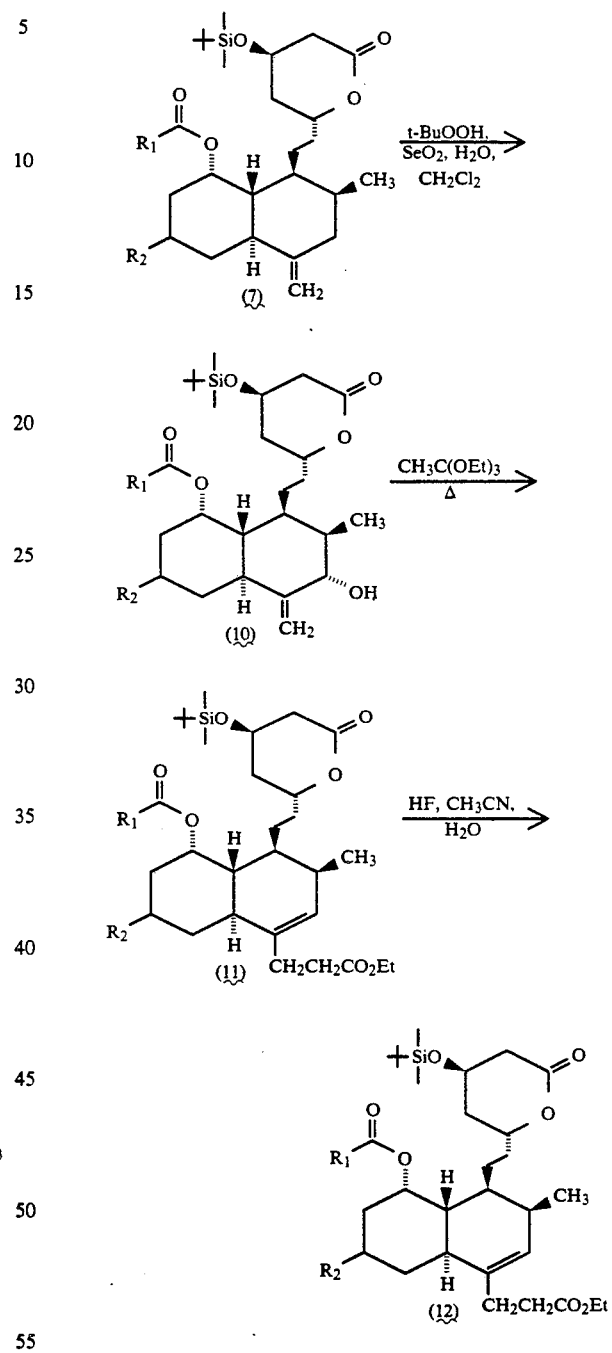

Starting material (1) is hydrogenated using a trialkylsilyl hydride in trifluoroacetic acid to yield monoene (2).

Monoene (2) is treated with a reagent suitable for protecting the alcohol group at the lactone 4-position. Examples of suitable reagents are trialkylsilyl chlorides, dialkylarylsilyl chlorides and dihydropyran.

Compound (3) is treated with m-chloroperoxybenzoic acid (MCPBA) to yield the epoxide (4) which is then reacted with boron trifluoride to form the ketone (5).

A Grignard reagent or an organolithium reagent is added to the ketone moiety to form compound (6).

Compound (6) was dehydrated employing methyl(carboxysulfamoyl)-triethyl ammonium hydroxide to yield exo-methylene intermediate (7). Intermediate (7) was treated with 10% Pd/C under hydrogen to form the 4-methyl compound (8). The hydroxy protecting group may be removed from compound (8) by treatment with tetrabutylammonium fluoride in acetic acid and THF to yield product (9).

As shown in Scheme 2 intermediate (5) can be directly converted to compound (7) by treatment with titanium tetrachloride, zinc and dibromomethane in THF. Compound (7) can be oxidized to intermediate (10) by treatment with tert-butyl hydroperoxide and selenium dioxide. Reaction of compound (10) with triethyl orthoacetate gave intermediate (11), which upon treatment with HF in aqueous acetonitrile gave product (12).

Where the reaction conditions of the above noted chemical transformations would be deleterious to the substituents in the 8-acyloxy moiety, the acetoxy group can be employed as a protecting group which after the elaboration of the naphthyl ring can be removed by hydrolysis to give the 8-hydroxy derivative which then can be acylated according to the general procedures described in U.S. Pat. No. 4,661,483.

Where the product formed by the above described synthetic pathways is not the desired form of that compound, then that product may be subjected to one or more further reactions such as hydrolysis, disilylation, ammonolysis or lactonization by conventional methods.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acide salts are basic amino acids, such as arginine, lysine, a,β-diaiminobutyric acid or ornithine.

Preferred amines to form amine salts include t-octylamine, dibenzylamine, ethylenediamine, morpholine, and tris(hydroxymethyl)aminomethane. Also preferred is ammonia to form the ammonium salt.

Esters are preferably the alkyl esters, such as the methyl, ethyl, propyl, isopropyl, butyl, isobutyl, or pentyl esters, of which the methyl ester is preferred. However, other esters such as phenyl-$C_{1-5}$alkyl may be employed if desired.

Metal salts of the carboxylic acids of formula (II) may be obtained by contacting a hydroxide, carbonate or similar solvent with the carboxylic acid of formula (II). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester(such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as diethyl ether and tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by metathesis.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example, a mineral acid (such as hydrochloric acid or sulphuric acid), a Lewis acid (for example boron trifluoride) or an acidic ion exchange resin. The solvent employed for this reaction is not critical, provided that it does not adversely affect the reaction; suitable solvents include the alcohol itself, benzene, chloroform, ethers and the like. Alternatively, the desire product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, a tetrahydrofuran, dimethylsulfoxide and acetone. Finally, esters may also be obtained from the lactone of formula (I) by reaction with an appropriate alkoxide in an absolute alkanol. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the in vitro protocol published in *J. Med. Chem.*, 28, p. 347-358 (1985).

For estimation of relative inhibitory potencies, compactin (i.e., mevastatin) was assigned a value of 100 and the $IC_{50}$ value of the test compound was compared with that of compactin determined simultaneously in the published in vitro protocol. Illustrative of the relative potency of the claimed compounds is that exhibited by compound (9′) of Example 1 which has a relative potency of 297.

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, or tablet, an injectable preparation or the like. It is usually desirable to use the oral route. Doses may be varied, depending on the age, severity, body weight and other conditions of human patients but daily dosage for adults is within a range of from about 10 mg to 2,000 mg (preferably 10 to 100 mg) which may be given in two to four divided doses.

The compounds of this invention may also be coadministered with pharmaceutically acceptable nontoxic cationic polymers capable of binding bile acids in a non-reabsorbable form in the gastrointestinal tract. Examples of such polymers include cholestyramine, coletipol and poly[methyl-(3-trimethylaminopropyl)iminotrimethylene dihalide]. The relative amount of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically-effective amount of the compounds of formulae (I) or (II) of pharmaceutical compositions thereof.

The following examples illustrates the present invention and as such are not to be considered as limiting the invention set forth in the claims appended hereto.

EXAMPLE 1

Preparation of 6(R)-[2-[8(S)-(2,2-dimethylbutyryloxy)2(S),4,6(S)-trimethyl-1,2,4a(S),5,6,7,8,8a(R) -octahydronaphthyl-1(S)]ethyl]-4(R)-hydroxy-3,4,5,6-tetrahydro-2H-pyran-2-one Step 1: Preparation of 6(R)-[2-[8(S)-(2,2-dimethylbutyryloxy) -2(S),6(S)-dimethyl-1,2,3,5,6,7,8,8a(R) -octahydronaphthyl-1(S)]ethyl]-4(R) -hydroxy-3,4,5,6-tetrahydro-2H-pyran-2-one (2)

Trifluoroacetic acid (36 ml) was added to a stirred solution of simvastatin (30 g, 71.7 mmol) and triethylsilane (24 ml, 0.18 mol) in methylene chloride at 0° C. The resulting mixture was stirred at 0° C. for 3 hours then warmed to ambient temperature and stirred for 15 hours. The reaction mixture was poured into ice/water mixture (600 ml) and extracted with ether (700 ml). The organic extract was washed with water (200 ml), sodium bicarbonate (prepared from dissolving 52 g of anhydrous sodium bicarbonate in 500 ml of water) and brine. After drying and filtration, the organic extract was concentrated to give a residue. Chromatography of the residue on a silica gel column and eluted with methylene chloride/acetone (20/1, v/v) removed the impurities. Continued elution with methylene chloride/acetone (10/1, v/v) afforded the desired 2' as a gummy oil: NMR (CDCl₃) δ 0.81 (3H, d, J=7 Hz), 0.83 (3H, t, J =7 Hz), 1.01 (3H, d, J=7 Hz), 1.13 (3H, s), 1.14 (3H, s), 2.62 (H, m of d, J=17 Hz), 2.76 (H, d of d, J=5, 17 Hz), 4.38 (H, m), 4.62 (H, m), 5.30 (H, m), 5.47 (H, m).

Step 2: Preparation of 6(R)-[2-[8(S)-(2,2-dimethylbutyryloxy) -2(S),6(S)-dimethyl-1,2,3,5,6,7,8,8a(R) -octahydronaphthyl-1(S)]ethyl]-4(R) (t-butyldimethylsilyloxy)-3,4,5,6,-tetrahydro -2H-pyran-2-one (3')

t-Butyldimethylsilyl chloride (8.6 g, 57 mmol) was added to a stirred solution of 2' (20 g, 48 mmol) and imidazole (9.8 g, 144 mmol) in DMF (90 ml). The resulting mixture was stirred at ambient temperature for 14 hours, then poured into cold water and extracted with ether. This ethereal extract was washed with 5% hydrochloric acid, brine, and sodium bicarbonate solution. After the drying and filtration, the filtrate was evaporated to afford the desired 3' as a gummy oil: NMR (CDCl₃) δ 0.08 (6H, s), 0.80 (3H, d, J=7 Hz), 0.82 (3H, t, J=7 Hz), 0.89 (9H, s), 1.00 (3H, d, J=7 Hz), 1.11 (3H, s), 1.12 (3H, s), 4.30 (H, m), 4.61 (H, m), 5.27 (H, m), 5.48 (H, m).

Step 3: Preparation of 6(R)-[2-[8(S)-(2,2-dimethylbutyryloxy) -2(S),6(S)-dimethyl-4,4a-epoxy -1,2,3,4,4a,5,6,7,8,8a(S)-decahydronaphthyl -1(S)]ethyl]-4(R)-(t-butyldimethylsilyloxy) -3,4,5,6,-tetrahydro-2H-pyran-2-one (4')

m-Chloroperoxybenzoic acid (22.6 g, 55% active, 72 mmol) powder was added in portions to a stirred solution of 3' (25.7 g, 48 mmol) in methylene chloride (200 ml). The resulting mixture was stirred at ambient temperature for 5 hours. The reaction mixture was diluted with ether (500 ml), then shaken with sodium hydroxide solution (0.25N, 750 ml). The aqueous layer was extracted with ether (300 ml). The combined extracts were washed with brine three times. After drying and filtration, the filtrate was concentrated to provide 4' as a gummy oil which was used in the next step without purification:

Step 4: Preparation of 6(R)-[2-[8(S)-(2,2-dimethylbutyryloxy) -2(S),6(S)-dimethyl-4-oxo-1,2,3,4,4a(S),5,6,7,8,8a(R)-decahydronaphthyl1(S)]ethyl]-4(R)-(t-butyldimethylsilyloxy)3,4,5,6,-tetrahydropyran-2-one (5')

Borontrifluoride etherate (11.4 ml, 93 mmol) was dropwise added at 0° C. to a stirred solution of 4' (26 g, 48 mmol) in ether (500 ml) under a nitrogen atmosphere. The resulting mixture was stirred at 0° C. for 1.5 hours, then quenched with sodium bicarbonate solution with vigorous stirring. The ethereal layer was separated and washed with sodium bicarbonate solution twice, then brine. After drying and filtration, the filtrate was evaporated to give a residue. Chromatography of the residue on a silica gel column eluted with 10% ethyl acetate in hexane removed the impurities. Further elution with 20% ethyl acetate in hexane produced the desired 5' as a solid: mp 134-6° C.; NMR (CDCl₃) δ 0.08 (6H, s), 0.79 (3H, d, J=7 Hz), 0.85 (3H, t, J=7 Hz), 0,87 (9H, s), 1.03 (3H, d, J=7 Hz), 1.18 (3H, s), 1.19 (3H, s), 2.10 (H, m), 2.28 (H, d of d, J=4, 18 Hz), 2.39 (H, m), 4.30 (H, m), 4.70 (H, m), 5.25 (H, m). Anal. Calcd for C₃₁H₅₄O₆Si: C, 67.59; H, 9.88. Found: C, 67.52; H, 9.89.

Step 5: Preparation of 6(R)-[2-[8(S)-(2,2-dimethylbutyryloxy) -2(S),4(R),6(S)-trimethyl-4-hydroxy-1,2,3,4,4a(S),5,6,7,8,8a(R)-decahydronaphthyl -1(S)]ethyl]-4(R)-(t,butyldimethylsilyloxy) -3,4,5,6,-tetrahydro-pyran-2-one (6')

Methylmagnesium bromide (3M in ether, 13.6 ml, 40.8 mmol) was added via a syringe under nitrogen to a stirred solution of 5' (13.8 g, 25 mmol) in ether (900 ml) at −15° C. The resulting mixture was stirred at −15° C. for 10 minutes, then warmed to ambient temperature and stirred for another 0.5 hours. The reaction mixture was recooled to −15° C., treated with 5% ammonium sulfate (300 ml) and stirred at −15° for 15 minutes, and finally poured into cold water and extracted with ether. The ethereal extract was washed with brine, dried, filtered and evaporated to give the desired 6' as a gummy oil: NMR (CDCl₃) δ 0.085 (3H, s), 0.09 (3H, s), 0.86 (3H, t, J=7 Hz), 0.89 (9H, s), 1.02 (3H, d, J =7 Hz), 1.08 (3H, d, J=7 Hz), 1.14 (3H, s), 1.16 (3H, s), 1.21 (3H, s), 4.29 (H, m), 5.57 (H, m), 5.22 (H, m).

Step 6: Preparation of 6(R)-[2-[8(S)-(2,2-dimethylbutyryloxy) -2(S),6,6(S)-trimethyl-1,2,4a(S),5,6,7,8-

,8a(R) -octahydronaphthyl-1(S)]ethyl]4(R) -(t-butyldimethylsilyloxy)-3,4,5,6,tetrahydro -2H-pyran-2-one (8')

The inner salt of methyl (carboxysulfamoyl)triethylammonium hydroxide (11.5 g, 42.4 mmol) was added to a stirred solution of 6' (13.5 g, 23.8 mmol) in toluene (410 ml). The resulting mixture was stirred at 65-70° C. under nitrogen for 1.5 hours. After cooling, the reaction was diluted with ether and washed with water (150 ml). The organic phase was separated, dried, filtered and concentrated in vacuo to yield a residue. This residue was purified on a silica gel column., Elution of the column with hexane/ethyl acetate (4/1, v/v) provided a 1.2/1 mixture of 7 and 8. This mixture was dissolved in ethanol (800 ml) and added to catalyst of 10% palladium on carbon (0.8·g). The reaction flask was topped with a 3-way stopcock with an attached balloon filled with hydrogen gas. The reaction flask was first connected to a house vacuum line to remove the air, then filled with hydrogen from the balloon. The reaction mixture was stirred at ambient temperature for 70 minutes. The catalyst was filtered off and the filtrate was evaporated to afford the desired 8 as a solid: mp 129-31° C.; NMR (CDCl$_3$) δ 0.08 (3H, s), 0.09 (3H, s), 0.82 (3H, d, J=7 Hz), 0.84 (3H, t, J=7 Hz), 0.90 (9H, s), 1.10 (3H, d, J=7 Hz), 1.14 (3H, s), 1.15 (3H, s), 1.67 (3H, s), 2.23 (H, m), 2.36 (H, t, J=12 Hz), 4.28 (H, m), 4.58 (H, m), 5.17 (H, m), 5.45 (H, d, J=6 Hz).

Step 7: Preparation of 6(R)-[2-[8(S)-(2,2-dimethylbutyryloxy) -2(S),4,6(S)-trimethyl-1,2,4a(S),5,6,7,8-,8a(R) -octahydronaphthyl-1(S)]ethyl]4(R) -hydroxy-3,4,5,6,-tetrahydro-2H-pyran-2-one (9')

Tetrabutylammonium fluoride solution (1M in THF, 50 ml, 50 mmol) was added to a stirred solution of 8' (8.9 g, 16.2 mmol) and acetic acid (4.2 g, 4 ml, 70 mmol) in THF (100 ml). The resulting mixture was stirred at ambient temperature for 60 hours, then poured into cold water and extracted with ether. The ethereal extract was washed with 5% sodium bicarbonate, dried, filtered and evaporated to give a residue. The residue was purified by chromatography on a silica gel column. Elution with methylene chloride/acetone (20/1, v/v) removed the impurities. Continued elution with methylene chloride/acetone (10/1, v/v) provided the desired 9' as a solid. This solid was triturated with ether/hexane and cooled in an acetone/ice bath for 0.5 hours. The purified 9' was collected by filtration as a white solid: mp 120-3° C.; NMR (CDCl$_3$) δ 0.82 (3H, d, J=7 Hz), 0.86 (3H, t, J=7 Hz), 1.10 (3H, d, J=7 Hz), 1.15 (3H, s), 1.16 (3H, s), 1.67 (3H, s), 2,23 (H, m), 2.37 (H, t, J=12 Hz), 2.61 (H, m of d, J=17 Hz), 2.73 (H, d of d, J =5, 17 Hz), 5.37 (H, m), 5.59 (H, m), 5.18 (H, m), 5.45 (H, d, J=6 Hz). Anal. Calcd. for C$_{26}$H$_{42}$O$_5$: C, 71.85; H, 9.74. Found: C, 71.61; H, 9.81.

EXAMPLE 2

Preparation of 6(R)-[2-[4-(2-ethoxycarbonyl)ethyl8(S) -(2,2-dimethylbutyryloxy)-2(S),6(S)-dimethyl1,2-,4a(S),5,6,7,8,8a(R) -octahydronaphthyl-1(S)]ethyl]-4(R)-hydroxy-3,4,5,6-tetrahydro-2H-pyran-2-one Step 1: Preparation of 6(R)-[2-[8(S)-(2,2-dimethylbutyryloxy) -4-methyleno-2(S),6(S)-dimethyl1,2,3,4-,4a(S),5,6,7,8,8a(R) -decahydronaphthyl-1(S)]ethyl]-4(R)-(t-butyldimethylsilyloxy) -3,4,5,6,-tetrahydro-2H-pyran-2-one (7')

Titanium tetrachloride solution (1M in methylene chloride, 0.4 ml, 0.4 mmol) was added via a syringe under nitrogen to a stirred mixture of zinc dust (108 mg, 1.64 mmol), methylene bromide (87 mg, 0.54 mmol) in THF (2 ml). The resulting mixture was stirred at ambient temperature for 20 minutes, followed by the addition of a solution of 5' (200 mg, 0.36 mmol) in THF (0.4 ml). The mixture was stirred at ambient temperature for 48 hours, diluted with ether, then washed successively with hydrochloric acid (0.5N) and sodium bicarbonate. After drying and filtration, the filtrate was evaporated to give a residue which was purified on a silica gel column. Elution of the column with 20% ethyl acetate in hexane provided the desired 7' as a gummy oil: NMR (CDCl$_3$) δ 0.075 (3H, s), 0.08 (3H, s), 1.72 (3H, d, J =7 Hz), 0.85 (3H, t, J=7 Hz), 0.89 (9H, s), 1.10 (3H, d, J=7 Hz), 1.18 (3H, s), 1.19 (3H, s), 4.28 (H, m), 4.58 (H, m), 4.68 (2H, s), 5.19 (H, m).

Step 2: Preparation of 6(R)-[2-[3(S)-hydroxy-8(S) -(2,2-dimethylbutyryloxy)-2(R),6(S)-dimethyl4-methyleno -1,2,3,4,4a(S),5,6,7,8,8a(R)-decahydronaphthyl -1(S)]ethyl]-4(R)-(t-butyldimethylsilyloxy) -3,4,5,6-tetrahydro-2H-pyran-2-one(10')

A stirred mixture of 7' (44 mg, 0.08 mmol) in methylene chloride (1.5 ml) and water (10 μl) was treated successively with t-butyl hydroperoxide (90% active, 18 μl, 0.17 mmol) and selenium dioxide (4.4 mg, 0.04 mmol). The resulting solution was stirred at 0° C. for 0.5 hours, then warmed to ambient temperature for 15 hours. Methylsulfide (10 μl) was added to the reaction mixture and stirred for 10 minutes, then poured into cold water and extracted with ether. The ethereal extract was dried, filtered and evaporated to leave a residue which was purified by chromatography. Elution of the column with 30% ethyl acetate in hexane afforded the desired 10' as a gummy oil: NMR (CDCl$_3$) δ 0.075 (3H, s), 0.08 (3H, s), 0.69 (3H, d, J=7 Hz), 0.85 (3H, t, J=7 Hz), 0.89 (9H, s), 1.10 (3H, d, J=7 Hz), 1.17 (3H, s), 1.19 (3H, s), 2.78 (H, t, J=12 Hz), 4.06 (H, m), 4.28 (H, m), 4.56 (H, m), 4.82 (H, m), 4.92 (H, m), 5.18 (H, m).

Step 3: Preparation of 6(R)-[2-[4-(2-ethoxycarbonyl)ethyl -8(S)-(2,2-dimethylbutyryloxy)-2(S),6(S) -dimethyl-1,2,4a(S),5,6,7,8,8a(R)-octahydronaphthyl -1(S)]ethyl]-4(R)-(t,butyldimethylsilyloxy) -3,4,5,6,-tetrahydro-2H-pyran-2-one (11')

A mixture of 10' (18 mg, 0.032 mmol) and freshly distilled triethylorthoacetate (0.5 ml) was heated at 150° C. under nitrogen for 15 minutes. After cooling, the mixture was diluted with water and extracted with ether. The extract was washed with saturated sodium bicarbonate and brine. After drying and filtration, the filtrate was concentrated and the residue was purified by chromatography. Elution of the column with 20% ethyl acetate gave the desired 11' as a gummy oil: NMR (CDCl$_3$) δ 0.075 (3H, s), 0.08 (3H, s), 0.82 (3H, d, J=7 Hz), 0.84 (3H, t, J =7 Hz), 0.88 (9H, s), 1.11 (3H, d, J=7 Hz), 1.14 (3H, s), 1.15 (3H, s), 1.26 (3H, t, J=7 Hz), 4.14 (2H, q, J=7 Hz), 4.28 (H, m), 4.58 (H, m), 5.17 (H, m), 5.46 (H, m).

Step 4: Preparation of 6(R)-[2-[4-(ethoxycarbonyl)ethyl -8(S)-(2,2-dimethylbutyryloxy)-2(S),6-(S) -dimethyl-1,2,4a(S),5,6,7,8,8a(R)-octahydronaphthyl -1(S)]ethyl]-4(R)-hydroxy-3,4, 5,6-tetrahydro-2H-pyran-2-one (12')

A solution of 11' (4 mg, 0.006 mmol) in acetonitrile (0.2 ml) was treated with hydrofluoric acid (0.125 ml, prepared from diluting 0.5 ml of 49% hydrofluoric acid with 9.5 ml of acetonitrile) at 0° C. The resulting mixture was stirred at 0° C. for 5 minutes, then warmed to ambient temperature and stirred for 3 hours. The reaction mixture was poured into cold water and extracted with ethyl acetate. The extract was washed with sodium bicarbonate and brine. After drying and filtration, the filtrate was concentrated and the residue was purified by chromatography. Elution of the column with 10% acetone in methylene chloride afforded the desired 12' as a gummy oil. nmr (CDCl$_3$) δ 0.81 (3H, d, J=7 Hz), 0.85 (3H, t, J=7 Hz), 1.12 (3H, d, J=7 Hz), 1.16 (3H, s), 1.17 (3H, s), 1.27 (3H, t, J=7 Hz), 2.60 (H, m of d, J=17 Hz), 2.73 (H, d of d, J=5,17 Hz), 4.15 (2H, g, J=7 Hz), 4.28 (H, m), 4.59 (H, m), 5.19 (H, m), 5.46 (H, m of d, J=6 Hz).

EXAMPLE 3

Preparation of 6(R)-[2-[8(S)-(2,2-dimethylbutyryloxy)-2(S),4,6(S)-trimethyl-1,2,3,4,4a(R),5,6,7,8,8a(R)-decahydronaphthyl-1(S)]ethyl]-4(R)-hydroxy-3,4,5,6-tetrahydro-2H-pyran-2-one To a solution of compound 9' in ethanol is added the catalyst 10% Pd/C, then hydrogenation on a parr shaker for 3 hours. After the removal of the catalyst by filtration, the filtrate is evaporated to afford the title compound.

EXAMPLE 4

Preparation of 6(R)-[2-[4-(2-ethoxycarbonyl)ethyl-8(S)-(2,2-dimethylbutyryloxy)-2(S),6(S)-dimethyl-1,2,3,4,a(R),5,6,7,8,8a(R)-decahydronaphthyl-1(S)]ethyl]-4-(R)-hydroxy-3,4,5,6-tetrahydro-2H-pyran-2-one The title compound is obtained from compound 12' via a similar procedure as that described in example 3.

EXAMPLE 5

Preparation of Ammonium Salts of Compounds II

The lactone (1.0 mmol) from Example 1, Step 7, is dissolved with stirring in 0.1N NaOH (1.1 mmol) at ambient temperature. The resulting solution is cooled and acidifeid by the dropwise addition of 1N HCl. The resulting mixture is extracted with diethyl ether and the extract washed with brine and dried (MgSO$_4$). The MgSO$_4$ is removed by filtration and the filtrate saturated with ammonia (gas) to give a gum which solidified to provide the ammonium salt.

EXAMPLE 6

Preparation of Alkali and Alkaline Earth Salts of Compounds II

To a solution of 44 mg of lactone from Example 1, Step 7, in 2 ml of ethanol is added 1 ml of aqueous NaOH (1 equivalent). After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 7

Preparation of Ethylenediamine Salts of Compounds II

To a solution of 0.05 g of the ammonium salt from Example 5 in 10 ml of methanol is added 0.04 ml of ethylenediamine. The methanol is stripped off under vacuum to obtain the desired ethylenediamine salt.

EXAMPLE 8

Preparation of Tris(hydroxymethyl)aminomethane Salts of Compounds II

To a solution of 202 mg of the ammonium salt from Example 5 in 5 ml of methanol is added a solution of 50 mg of tris(hydroxymethyl)aminomethane in 5 ml of methanol. The solvent is removed in vacuo to afford the desired tris(hydroxymethyl)aminomethane salt.

EXAMPLE 9

Preparation of L-Lysine Salts of Compounds II

A solution of 0.001 mole of L-lysine and 0.0011 mole of the ammonium salt from Example 5 in 15 ml of 85% ethanol is concentrated to dryness in vacuo to give the desired L-lysine salt.

Similarly prepared are the L-arginine, L-ornithine, and N-methylglucamine salts.

EXAMPLE 10

Preparation of Tetramethylammonium Salts of Compounds II

A mixture of 69 mg of ammonium salt from Example 5 in 2 ml of methylene chloride and 0.08 ml of 24% tetramethylammonium hydroxide in methanol is diluted with ether to yield the desired tetramethylammonium salt.

EXAMPLE 11

Preparation of Methyl Esters of Compounds II

To a solution of 400 mg of lactone from Example 1, Step 7, in 100 ml of absolute methanol is added 10 ml 0.1M sodium methoxide in absolute methanol. This solution is allowed to stand at room temperature for one hour, then is diluted with water and extracted twice with ethyl acetate. The organic phase is separated, dried (Na$_2$SO$_4$), filtered and evaporated in vacuo to yield the desired methyl ester.

In like manner, by the use of equivalent amounts of propanol, butanol, isobutanol, t-butanol, amylalcohol, isoamylalcohol, 2,2-dimethylaminoethanol, benzylalcohol, phenethanol, 2-acetamidoethanol and the like, the corresponding esters are obtained.

EXAMPLE 12

Preparation of Free Dihydroxy Acids

The sodium salt of the compound II from Example 6 is dissolved in 2 ml of ethanol-water (1:1; v:v) and added to 10 ml of 1N hydrochloric acid from which the dihydroxy acid is extracted with ethyl acetate. The organic extract is washed once with water, dried (Na$_2$SO$_4$), and evaporated in vacuo with a bath temperature not exceeding 30° C. The dihydroxy acid derivative derived slowly reverts to the corresponding, parent lactone on standing. The compound can maintained in the dihydroxy acid form by increasing the pH above 7.0.

EXAMPLE 13

As a specific embodiment of a composition of this invention, 20 mg of lactone from Example 1, Step 7, is formulated with sufficient finely divided lactose to provide a total amount of 580 to 590 mg to fill a size 0, hard-gelatin capsule.

What is claimed is:

1. A compound of formula (II):

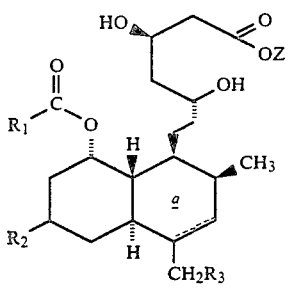
(II)

R₁ is:
(1) $C_{1-10}$ alkyl;
(2) substituted $C_{1-10}$ alkyl in which one or more substituent(s) is
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y,
 (i) $C_{1-10}$ alkylS(O)$_n$,
 (j) $C_{3-8}$ cycloalkylS(O)$_n$,
 (k) phenylS(O)$_n$,
 (l) substituted phenylS(O)$_n$ in which the substituents are X and Y, and
 (m) oxo,
 (n) nitrile,
 (o) NR₄R₅,
 (p) CONR₄R₅;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is
 (a) $C_{1-10}$ alkyl
 (b) substituted $C_{1-10}$ alkyl in which the substituent is
  (i) halogen,
  (ii) hydroxy,
  (iii) $C_{1-10}$ alkoxy,
  (iv) $C_{1-5}$ alkoxycarbonyl,
  (v) $C_{1-5}$ acyloxy,
  (vi) phenyl,
  (vii) substituted phenyl in which the substituents are X and Y
  (viii) $C_{1-10}$ alkylS(O)$_n$,
  (ix) $C_{3-8}$ cycloalkylS(O)$_n$,
  (x) phenylS(O)$_n$,
  (xi) substituted phenylS(O)$_n$ in which the substituents are X and Y, and
  (xii) oxo,
 (c) $C_{1-10}$ alkylS(O)$_n$,
 (d) $C_{3-8}$ cycloalkylS(O)$_n$,
 (e) phenylS(O)$_n$,
 (f) substituted phenylS(O)$_n$ in which the substituents are X and Y,
 (g) halogen,
 (h) hydroxy,
 (i) $C_{1-10}$ alkoxy,
 (j) $C_{1-5}$ alkoxycarbonyl,
 (k) $C_{1-5}$ acyloxy,
 (l) phenyl, and
 (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from the group consisting of:
 (a) piperidinyl,
 (b) pyrrolidinyl,
 (c) piperazinyl;
R₂ is H or CH₃;
R₃ is selected from:
 (a) hydrogen,
 (b) halogen,
 (c) hydroxy,
 (d) $C_{1-15}$ alkyl,
 (e) substituted $C_{1-5}$ alkyl in which the substituent is selected from:
  (1) OH,
  (2) halogen,
  (3) trifluoromethyl,
  (4) $C_{1-3}$ alkoxy,
  (5) $C_{1-3}$ alkylcarbonyloxy,
  (6) phenylcarbonyloxy,
  (7) $C_{1-3}$ alkoxycarbonyl,
  (8) phenyloxycarbonyl,
  (9) NR₄R₅,
  (10) CONR₄R₅;
 (f) $C_{2-6}$ alkenyl,
 (g) phenyl substituted with X and Y,
 (h) $C_{1-5}$ alkylS(O)$_n$,
 (i) phenylS(O)$_n$,
 (j) $C_{1-3}$ alkoxycarbonyl,
 (k) NR₄R₅,
 (l) CONR₄R₅,
 (m) $C_{1-3}$ alkoxy,
 (n) $C_{1-3}$ alkylcarbonyloxy,
 (o) phenylcarbonyloxy;
R₄ and R₅ are independently selected from:
 (a) $C_{1-5}$ alkyl,
 (b) substituted phenyl in which the substituents are X and Y;
X and Y are independently selected from:
 (a) OH,
 (b) halogen,
 (c) trifluoromethyl,
 (d) $C_{1-3}$alkoxy,
 (e) $C_{1-3}$alkylcarbonyloxy,
 (f) phenylcarbonyloxy,
 (g) $C_{1-3}$alkoxycarbonyl,
 (h) phenyloxycarbonyl,
 (i) hydrogen,
 (j) $C_{1-5}$alkyl;
Z is selected from
 (1) hydrogen;
 (2) $C_{1-5}$alkyl;
 (3) substituted $C_{1-5}$ in which the substituent is selected from (a) phenyl,
(b) dimethylamino, and
(c) acetylamino, and
(4) 2,3-dihydroxypropyl;
a is a single bond or a double bond; halogen is Cl or F; n is 0, 1 or 2; or a pharmaceutically acceptable salt thereof.

2. A compound of claim 1 wherein:
$R_1$ is selected from:
(1) $C_{1-10}$ alkyl;
(2) substituted $C_{1-10}$ alkyl in which one or more substituent(s) is selected from
(a) halogen,
(b) hydroxy,
(c) $C_{1-10}$ alkoxy,
(d) $C_{1-5}$ alkoxycarbonyl,
(e) $C_{1-5}$ acyloxy,
(f) $C_{3-8}$ cycloalkyl,
(g) phenyl,
(h) substituted phenyl in which the substituents are X and Y,
(i) $C_{1-10}$ alkylS(O)$_n$,
(j) nitrile,
(k) $NR_4R_5$,
(l) $CONR_4R_5$,
(m) oxo;
(3) $C_{3-8}$ cycloalkyl;
(4) substituted $C_{3-8}$ cycloalkyl in which one substituent is selected from
(a) $C_{1-10}$ alkyl,
(b) substituted $C_{1-10}$ alkyl in which the substituent is selected from
(i) halogen,
(ii) hydroxy,
(iii) $C_{1-10}$ alkoxy
(iv) $C_{1-5}$ acyloxy,
(v) $C_{1-5}$ alkoxycarbonyl,
(vi) phenyl,
(vii) substituted phenyl in which the substituents are X and Y, and
(viii) oxo,
(c) halogen,
(d) hydroxy,
(e) $C_{1-10}$ alkoxy,
(f) $C_{1-5}$ alkoxycarbonyl,
(g) $C_{1-5}$ acyloxy,
(h) phenyl,
(i) substituted phenyl in which the substituents are X and Y;
(5) phenylamino;
(6) substituted phenylamino in which the substituents are X and Y;
(7) phenyl$C_{1-10}$alkylamino; and
(8) substituted phenyl $C_{1-10}$ alkylamino in which the substituents are X and Y,
(9) $C_{2-10}$ alkenyl;
$R_3$ is:
(a) hydrogen;
(b) hydroxy,
(c) $C_{1-5}$ alkyl,
(d) substituted $C_{1-5}$ alkyl in which the substitutent is selected from:
(1) OH,
(2) $C_{1-3}$ alkoxy,
(3) $C_{1-3}$ alkylcarbonyloxy,
(4) phenylcarbonyloxy,
(5) $C_{1-3}$ alkoxycarbonyl,
(6) phenyloxycarbonyl;
(e) phenyl substituted with X and Y;
(f) $C_{1-3}$ alkoxy,
(g) $C_{1-3}$ alkylcarbonyloxy,
(h) phenylcarbonyloxy.
X and Y independently are:
(a) OH,
(b) F,
(c) trifluoromethyl,
(d) $C_{1-3}$ alkoxy,
(e) hydrogen,
(f) $C_{1-5}$ alkyl.

3. A compound of claim 2 wherein:
$R_1$ is $C_{1-10}$ alkyl;
$R_2$ is $CH_3$, and
$R_3$ is:
(a) hydrogen; or
(b) $C_{1-5}$ alkyl,
(c) substituted $C_{1-5}$alkyl in which the substituent is selected from:
(1) $C_{1-3}$alkoxy carbonyl,
(2) hydroxy,
(3) oxo.

4. A hypocholesterolemic, hypolipidemic pharmaceutical composition comprising a pharmaceutically acceptable carrier and a therapeutically effective amount of a compound of claim 1.

5. A hypocholesterolemic, hypolipidemic pharmaceutical composition comprising a therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

6. A method of treating hypercholesterolemia comprising the administration to a subject in need of such treatment and therapeutically effective amount of a compound of claim 1.

7. The compound of claim 3 selected from the group consisting of:
(1) 7-[1,2,4a(S),5,6,7,8,8a(R)-octahydro -2(S),4,6(S)-trimethyl-8(S)-(2,2-dimethylbutyryloxy)-1(S) -naphthyl]-3(R),5(R)-dihydroxyheptanoic acid;
(2) 7-[1,2,4a(S),5,6,7,8,8a(R)-octahydro-2(S), 6(S)-dimethyl-4-(2-ethoxycarbonyl)ethyl-8(S)-(2,2-dimethylbutyryloxy) -1(S)-naphthyl]-3(R),5(R)-dihydroxyheptanoic acid;
(3) 7-[1,2,4a(S),5,6,7,8,8a(R)-octahydro-2(S), 4,6,(S)-trimethyl-8(S)-(2-methylbutyryloxy)-1(S)-naphthyl]3(R),5(R) -dihydroxyheptanoic acid; and
(4) 7-[1,2,4a(S),5,6,7,8,8a(R)-octahydro-2(S),6(S) -dimethyl-4-(2-ethoxycarbonyl)ethyl-8(S)-(2-methylbutyryloxy) -1(S)-naphthyl]-3(R),5(R)-dihydroxyheptanoic acid; and esters thereof.

8. The composition of claim 4 in which the compound is selected from:
(1) 7-[1,2,4a(S),5,6,7,8,8a(R)-octahydro -2(S),4,6(S)-trimethyl-8(S)-(2,2-dimethylbutyryloxy)-1(S) -naphthyl]-3(R),5(R)-dihydroxyheptanoic acid;
(2) 7-[1,2,4a(S),5,6,7,8,8a(R)-octahydro-2(S), 6(S)-dimethyl-4-(2-ethoxyarbonyl)ethyl-8(S)-(2,2-dimethylbutyryloxy) -1(S)-naphthyl]-3(R),5(R)-dihydroxyheptanoic acid;
(3) 7-[1,2,4a(S),5,6,7,8,8a(R)-octahydro-2(S), 4,6,(S)-trimethyl-8(S)-(2-methylbutyryloxy)-1(S)-naphthyl]3(R),5(R) -dihydroxyheptanoic acid; and
(4) 7-[1,2,4a(S),5,6,7,8,8a(R)-octahydro-2(S),6(S) -dimethyl-4-(2-ethoxycarbonyl)ethyl-8(S)-(2-methylbutyryloxy) -1(S)-naphthyl]-3(R),5(R)-dihydroxyheptanoic acid; and esters thereof.

9. The method of claim 6 in which the compound is selected from:
(1) 7-[1,2,4a(S),5,6,7,8,8a(R)-octahydro -2(S),4,6(S)-trimethyl-8(S)-(2,2-dimethylbutyryloxy)-1(S) -naphthyl]-3(R),5(R)-dihydroxyheptanoic acid;
(2) 7-[1,2,4a(S),5,6,7,8,8a(R)-octahydro-2(S), 6(S)-dimethyl-4-(2-ethoxycarbonyl)ethyl-8(S)-(2,2-dimethylbutyryloxy) -1(S)-naphthyl]-3(R),5(R)-dihydroxyheptanoic acid;
(3) 7-[1,2,4a(S),5,6,7,8,8a(R)-octahydro-2(S), 4,6,(S)-trimethyl-8(S)-(2-methylbutyryloxy)-1(S)-naphthyl]3(R),5(R) -dihydroxyheptanoic acid; and
(4) 7-[1,2,4a(S),5,6,7,8,8a(R)-octahydro-2(S),6(S) -dimethyl-4-(2-ethoxycarbonyl)ethyl-8(S)-(2-methylbutyryloxy) -1(S)-naphthyl]-3(R),5(R)-dihydroxyheptanoic acid; and esters thereof.

* * * * *